(12) United States Patent
Nakamura et al.

(10) Patent No.: US 11,344,371 B2
(45) Date of Patent: May 31, 2022

(54) VISUALIZATION OF THREE-DIMENSIONAL IMAGE DATA ON A TWO-DIMENSIONAL IMAGE

(71) Applicant: Canon U.S.A., Inc., Melville, NY (US)

(72) Inventors: Hitoshi Nakamura, Boston, MA (US); Barret Daniels, Cambridge, MA (US); Antonio Bonillas Vaca, Boston, MA (US); Christopher Wayne Thurrott, Townsend, MA (US); Morgan Carlson Rudolph, Saint Joseph, MI (US)

(73) Assignee: Canon U.S.A., Inc., Melville, NY (US)

( * ) Notice: Subject to any disclaimer, the term of this patent is extended or adjusted under 35 U.S.C. 154(b) by 198 days.

(21) Appl. No.: 16/591,332

(22) Filed: Oct. 2, 2019

(65) Prior Publication Data
US 2020/0121393 A1 Apr. 23, 2020

Related U.S. Application Data

(60) Provisional application No. 62/748,168, filed on Oct. 19, 2018.

(51) Int. Cl.
*A61B 34/10* (2016.01)
*G06T 7/00* (2017.01)
(Continued)

(52) U.S. Cl.
CPC .............. *A61B 34/10* (2016.02); *A61B 34/20* (2016.02); *A61B 34/25* (2016.02); *G06T 7/0014* (2013.01); *A61B 2034/104* (2016.02); *A61B 2034/107* (2016.02); *A61B 2034/2051* (2016.02); *A61B 2034/2065* (2016.02);
(Continued)

(58) Field of Classification Search
CPC . G06F 3/04845; A61B 17/3403; A61B 34/25; A61B 34/10; A61B 34/20; A61B 2034/108; A61B 2034/2065; A61B 2034/2051; A61B 2017/00973; A61B 2090/363; A61B 2034/2059; A61B 2034/102; A61B 2034/104; A61B 2034/107; G06T 7/0014; G06T 19/003;
(Continued)

(56) References Cited

U.S. PATENT DOCUMENTS 9,222,966 B2  12/2015 Amanuma
9,222,996 B2  12/2015 Fujimoto et al.
(Continued)

FOREIGN PATENT DOCUMENTS

JP    2003-10149 A    1/2003
JP    2014-526946 A   10/2014
(Continued)

OTHER PUBLICATIONS

Office Action issued in related application No. JP2019-189926 dated Feb. 9, 2021.

*Primary Examiner* — Brenda C Bernardi
(74) *Attorney, Agent, or Firm* — Canon U.S.A., Inc., IP Division

(57) ABSTRACT

The present disclosure relates generally to medical imaging and, more particularly to systems, methods, and devices for planning and carrying out minimally invasive procedures using external devices for needle guidance and the display and manipulation of the image set when planning and performing the procedure.

17 Claims, 7 Drawing Sheets

(51) Int. Cl.
*A61B 34/00* (2016.01)
*A61B 34/20* (2016.01)

(52) U.S. Cl.
CPC ............... *G06T 2207/10081* (2013.01); *G06T 2207/10088* (2013.01); *G06T 2207/10132* (2013.01)

(58) Field of Classification Search
CPC . G06T 2207/10081; G06T 2207/10132; G06T 2207/10088
See application file for complete search history.

(56) References Cited

U.S. PATENT DOCUMENTS

| | | | |
|---|---|---|---|
| 9,269,141 B2 | 2/2016 | Wiemker et al. | |
| 9,710,146 B2 | 7/2017 | Tokunaga et al. | |
| 9,867,667 B2 | 1/2018 | Fujimoto et al. | |
| 9,867,673 B2 | 1/2018 | Onuma et al. | |
| 10,163,228 B2 | 12/2018 | Kim et al. | |
| 10,499,879 B2 | 12/2019 | Veronesi et al. | |
| 10,614,335 B2 | 4/2020 | Cohen-Solal et al. | |
| 2011/0007071 A1 | 1/2011 | Pfister | |
| 2014/0027597 A1 | 1/2014 | Farris | |
| 2015/0279061 A1* | 10/2015 | Kutsuna | G06T 7/0012 382/131 |
| 2015/0356245 A1* | 12/2015 | Kozuka | G06F 3/0488 705/2 |
| 2016/0007406 A1 | 1/2016 | Yi et al. | |
| 2017/0000058 A1 | 1/2017 | Huskowska et al. | |
| 2017/0003055 A1 | 1/2017 | De Luca | |
| 2017/0007162 A1 | 1/2017 | Choi et al. | |
| 2017/0017245 A1 | 1/2017 | Jovanovic | |
| 2017/0337336 A1* | 11/2017 | Weidner | A61B 6/502 |
| 2019/0000859 A1 | 1/2019 | Shi et al. | |
| 2019/0005687 A1* | 1/2019 | Weingarten | G06T 19/00 |
| 2019/0008591 A1* | 1/2019 | Desai | A61B 34/25 |
| 2019/0046232 A1 | 2/2019 | Tokuda et al. | |
| 2019/0151023 A1 | 5/2019 | Lu et al. | |
| 2019/0151026 A1 | 5/2019 | Lu et al. | |
| 2019/0282301 A1 | 9/2019 | Bonillas Vaca | |
| 2020/0121287 A1 | 4/2020 | Nakamura | |
| 2020/0121392 A1 | 4/2020 | Daniels | |

FOREIGN PATENT DOCUMENTS

| | | |
|---|---|---|
| WO | 2017/180643 A1 | 10/2017 |
| WO | 2018/075671 A1 | 4/2018 |
| WO | 2018175094 A1 | 9/2018 |

* cited by examiner 350  300  400

VISUALIZATION OF THREE-DIMENSIONAL IMAGE DATA ON A TWO-DIMENSIONAL IMAGE

CROSS-REFERENCE TO RELATED APPLICATION(S)

This application relates, and claims priority, to U.S. Patent Application Ser. No. 62/748,168, filed Oct. 19, 2018, the entire disclosure of which is incorporated by reference herein in its entirety.

FIELD OF THE INVENTION

The present disclosure relates generally to medical imaging and, more particularly to systems, methods, and devices for planning and carrying out minimally invasive procedures using external devices for needle guidance.

BACKGROUND OF THE INVENTION

Minimally invasive medical procedures are becoming increasingly popular in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

Medical images assist physicians in planning, performing, and post-operative analysis of minimally invasive and other procedures. Some imaging modalities that are useful include ultrasound imaging, computed tomography (CT), and magnetic resonance imaging (MRI). Medical images can also be used to assist in navigating various instruments relative to the patient while performing a procedure.

During planning, for minimally invasive image-guided needle interventions (biopsy, ablation therapy, etc.), a target lesion or anatomy is usually identified in medical images of modalities such CT, MRI, etc. An insertion point on the skin surface is also usually identified in the medical images to plan the needle trajectory. To aid in directing the needle along the planned trajectory a guidance device may be used, positioned on or near the patient skin. The device geometry plus the length of the needle will place constraints on the reachable area, so a mental picture is formed based on knowledge of the device, experience and measurements on the image data to determine whether the target is reachable from the chosen insertion point. During a procedure using a guidance device, the device is placed on the patient and new images are acquired, on which the device can be identified and registered to the image space. It can then be confirmed whether the target is reachable.

However, the medial images are generally scanned in a cross-section relative to the patient anatomy (e.g., the patient lies on the gantry within a CT or MRI bore) and the cross sectional images are obtained without reference to the relative location of the target lesion and the skin entry point. Thus, when viewing a two-dimensional image on the screen, it can be difficult to visualize and understand the relationship between the target lesion, the skin entry point, and any critical structures or other features that could affect the intervention.

Thus, in conventional systems, there is limited ability to plan, perform, and analyze the effectiveness of the procedure with sufficient simplicity, accuracy, no provision for simulating the device placement in the imaging software during planning for evaluating target reachability. Thus, before the needle guidance device is placed on the patient, imaged and registered to the image space, it is difficult to be certain that the target point is reachable from the chosen insertion point using the device.

While U.S. Pat. No. 9,710,146; U.S. Pat. Pub. 2011/0007071 and others have provided systems and methods for image display control that supports a user in selecting an image of interested from among a three-dimensional data set, it does not allow for a simple and intuitive way of planning and carrying out minimally invasive procedures for needle guidance.

Thus, there is need for devises, systems, and methods to overcome the problems as discussed above.

SUMMARY OF THE INVENTION

Accordingly, it is a broad object of the present disclosure to provide devices, systems, and methods to allow a clinician to easily visualize 3D images on a 2D display to provide planning, performance, and evaluation techniques.

The present disclosure provides an image processing apparatus and a method of use for supporting a needle placement process, planning, or assessment comprising a processor that operates to: acquire a three-dimensional image set comprising a stack of two-dimensional image slices, the three-dimensional image set; acquire the location of at least one region of interest or at least one target point in the three-dimensional image set; acquire the location of at least one insertion point in the three-dimensional image set; cause a display to display a first image slice from the three-dimensional image set; and cause the display to display, concurrent with the first image slice, an indicator bar, wherein the indicator bar indicates: the location of the first two-dimensional image slice within the three-dimensional image set, the location of the at least one region of interest or at least one target point within the three-dimensional image set, and the location of the insertion point with the three-dimensional image set.

Also provided are methods for visualizing, performing planning or treatment for a percutaneous probe treatment, by using the apparatus and/or processer as described herein. Other embodiments include a server storing an imaging application having instructions that, when executed by a processor, cause the server to perform the methods as described herein. Yet other embodiments include a non-transitory computer-readable storage medium storing an imaging application to cause an imaging server to perform the methods as described herein.

In one or more embodiments, the devices as described in U.S. Pat. Nos. 9,222,966, 9,867,667, 9,867,673, U.S. Pat. Pub. 2014/0275978, U.S. Pat. Pub. 2016/0074063, U.S. Pat. Pub. 2017/0071626, U.S. Pat. Pub. 2017/0030557, U.S. Pat. Pub. 2017/0000581, U.S. Pat. Pub. 2017/0172458, International Pub. WO2017/180643, and International Pub. WO2018/075671, each of which are incorporated by reference herein in their entirety may be used in conjunction with the planning, performance, and evaluation apparatuses and systems, and methods as described herein.

In accordance with one or more embodiments of the present disclosure, visualizing, planning, performance, and evaluation apparatuses and systems, and methods and storage mediums may operate to characterize and/or treat biological objects, such as, but not limited to, lesions, tumors, critical structures, etc.

In accordance with at least another aspect of the present disclosure, the planning, performance, and evaluation technique(s) systems and methods discussed herein may be employed to reduce the cost of at least one of manufacture and maintenance of planning, performance, and evaluation devices, systems and storage mediums by reducing or minimizing a number of components therein to cut down cost.

According to other aspects of the present disclosure, one or more additional devices, one or more systems, one or more methods and one or more storage mediums for planning, performance, and evaluation are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

Exemplary embodiments are described below with reference to the drawings. The present invention provides for improved visualization of image date where the image date is two-dimensional slices of three-dimensional (3D) image set. While many clinicians are comfortable paging through the various slices to obtain an understanding of the region of interest and surrounding tissue, as the planning and/or procedures become more complicated, the ability to visualize information from the 3D image set when viewing a two-dimensional (2D) image become important.

Figure 1:
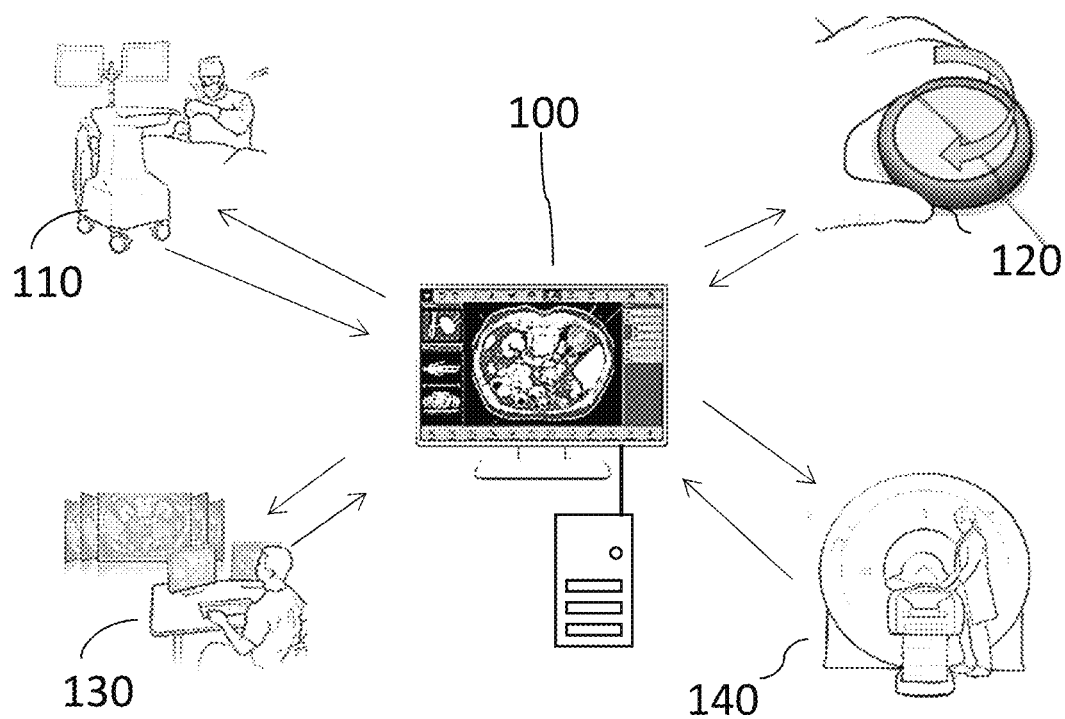
FIG. 1 is a schematic diagram showing an embodiment of a system for performing a needle placement in accordance with one or more aspects of the present disclosure.

For example, in some embodiments, a clinician will plan, perform, and/or evaluate performance. FIG. 1 illustrates a system with displayed image data 100, a model system and cart 110, a device model 120, and registered device model 130 that can be overlaid on the displayed image data 100. In some embodiments, the planning image data 100 is a three-dimensional image set obtained from an imaging system (CT, MRI, etc.) 140. In some preferred embodiments, the three-dimensional image set is a medical image data set of an object that needs to be diagnosed and/or treated. The image software can allow for planning and assistance or automation in a diagnostic and/or treatment procedure by defining a needle trajectory by setting target and insertion point locations. Additionally, the imaging software may calculate an insertion depth based on the needle trajectory and the displayed image data 100. In some embodiments, the imaging software includes a device model 120. The device model 120 is a 3D model representation of the physical guidance device to be used in a procedure. The physical guidance device may be any suitable device for guiding a needle, probe or other medical device during preparation or performance of the procedure. The needle may be any suitable size or length needle for the procedure. In some embodiments, data corresponding to each needle of a plurality of needles or other medical device(s) is/are stored in the computing system as respective device models included in the imaging software.

Figure 2:
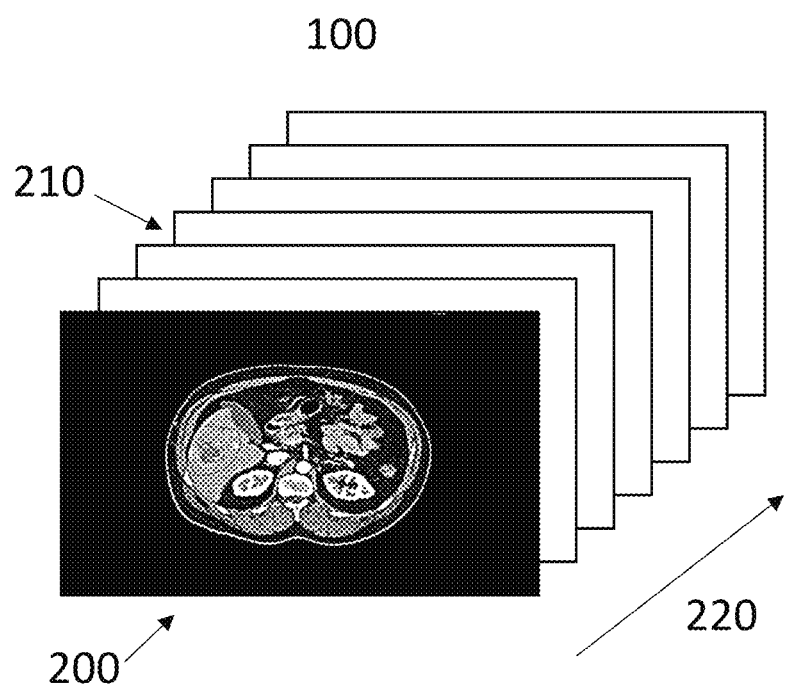
FIG. 2 is schematic of multiple slice images in a CT scan.

The image data 100 comprises the 2D image presented to the clinician 200 as well as a 3D data set 210 extending along an axial direction 220, which generally corresponds, to the patient's bed (FIG. 2).

Figure 3A:
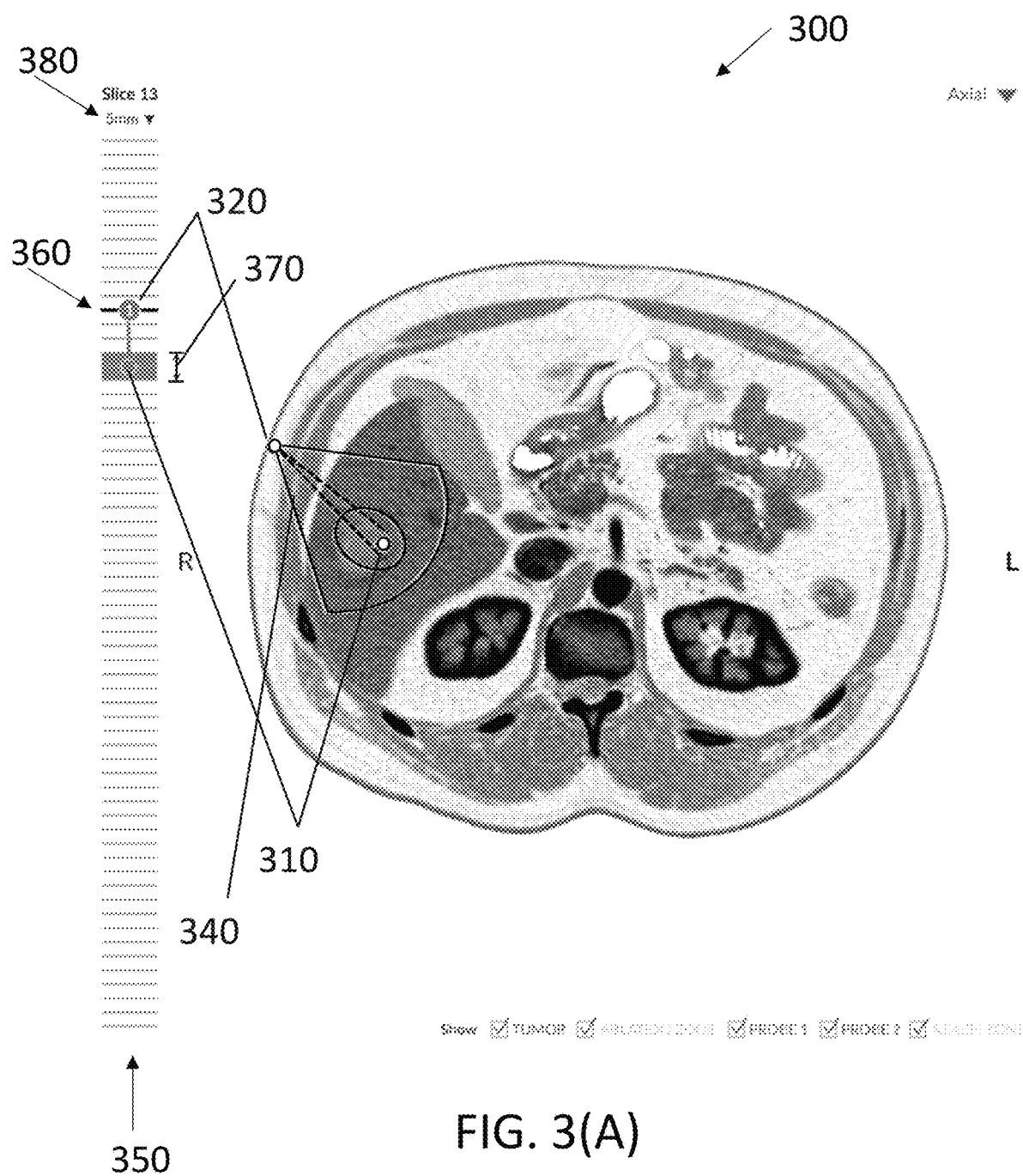
FIG. 3(A) is an illustration of a CT scan including an overlay providing 3D information and an indicator bar.
Figure 3B:
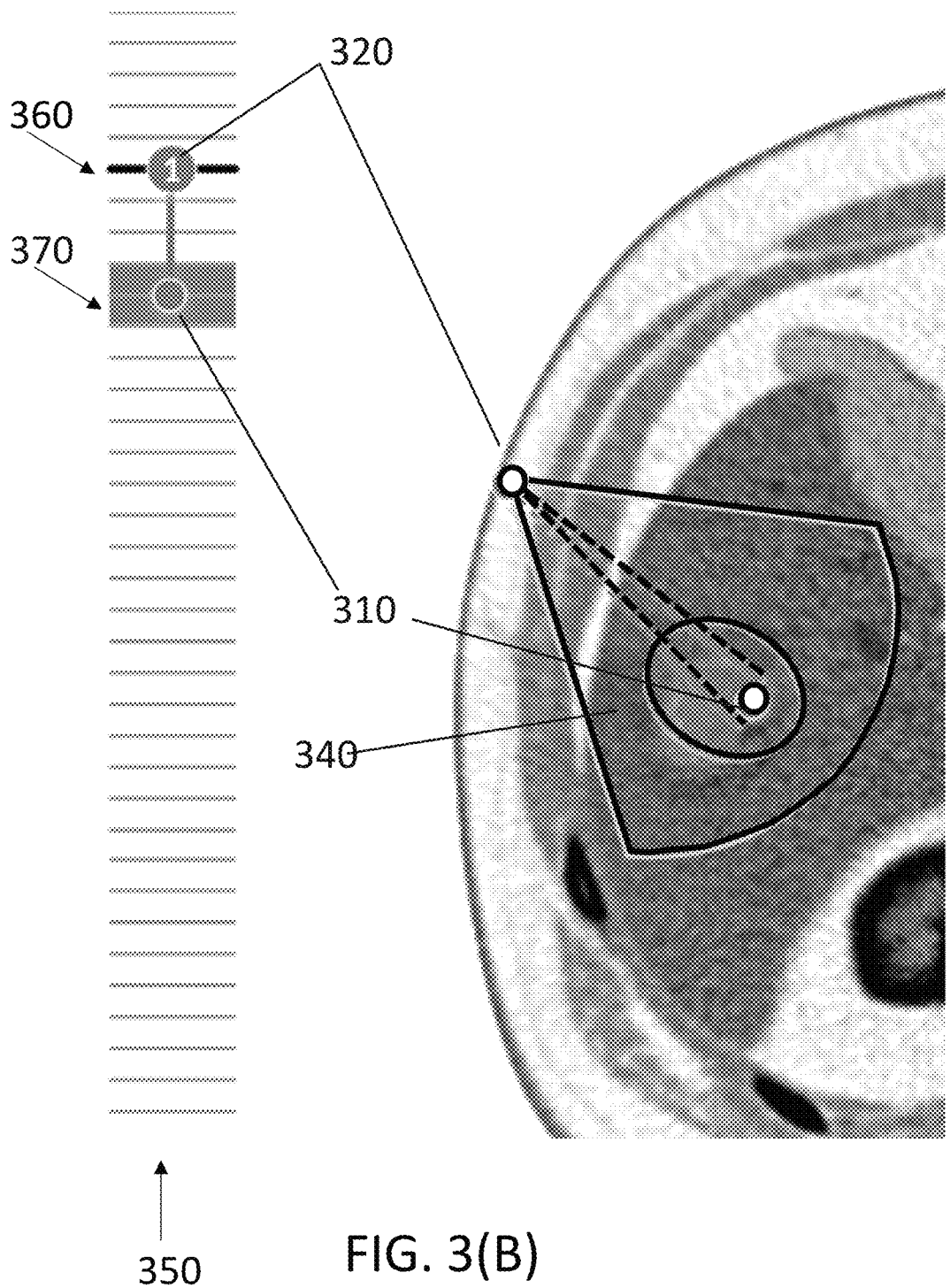
FIG. 3(B) is an expansion of the sidebar and region of interest from FIG. 3(A).

FIGS. 3(A) and 3(B) provides a 2D CT image of a patient 300. Both a target point 310 and an insertion point 320 are identified in this image. A probe trajectory 340 is defined by the line between the target point 310 and the insertion point 320. The broken line provides the probe trajectory in other 2D slices 340.

On the side of the image 2D image 300, an indicator bar 350 is provided where the location of the slice image in the 3D image data set is indicated. In addition to showing the location of the visualized slice 360 with a thicker line (or with a different color, a marker, a blinking line, etc.), the depth of the region of interest 370 through multiple slices is shown in the side bar as well. This facilitates easy viewing, planning, and procedure, particularly for describing depth information, since the 2D image does not facilitate an easy understanding of the depth of various features within the image when the doctor or technician is viewing the 3D image set by viewing the 2D image slices sequentially. For the CT image slice of FIG. 3(A), the thickness of the slice is indicated by the spacing of the lines on the indicator bar 350, where the number of slices within the 3-dimensional image set is indicated by the number of horizontal lines in the status bar.

Thus, imaging apparatus and software allows for, for example, the planning, performance, and evaluation of the insertion of one or more biopsy or ablation probes. The software can load images scanned by an imaging system 140 (e.g., a CT scanner) and shows them on a display 100. The clinician, such as a doctor or technician can set planning information (e.g. insertion point, target point).

To display the slice image 300, the imaging software draws one of the axial slices scanned by the imaging system 140 on a display. The imaging software also draws an indicator bar 350, which provides information as to which axial slice is displayed. In this embodiment, the bar 350 is overlaid on left side of the slice. However, in other embodiments, the indicator bar 350 may be located, for example, above, below, or to the right of the slice image. Additionally, in some embodiments, the location of the indicator bar 350 may be moved by the user via the input device (e.g., by clicking or dragging the indicator bar.) In other embodiments, the content of the indicator bar 350 may be zoomed in or out to see more or less of the full bar length (i.e., more or less of the scope of the three-dimensional image set).

The image 300 being displayed may be controlled by the user with an input device. The indicator bar 350 provide the location of the slice 360 within the 3D image data provided by the imaging system 140 by marking the slice 360 within the full three-dimensional image set shown by the indicator bar 350. This feature enables users to know which image slice 300 is shown in the display. Software may also show slice information 380 (e.g. thickness, the number of slices) as shown in FIG. 3(A) in the upper left. The input device may be, for example, a mouse, a touch screen, a keyboard, keypad, microphone, monitor, speaker, still camera, stylus, tablet, touch screen, trackball, video camera or other movement sensor, etc.

In use, as the user scrolls or otherwise moves through various slice images 300, the position of the visualized slice 360 moved along the indicator bar 350 to show where the slice is relative to the other slice images. As the user scrolls along the indicator bar 350 using the input device, the slide image 300 will change to correspond to the slice image of the slice indicated on the indicator bar 350 as the visualized slice 360. Similarly, if additional two-dimensional images are displayed, the images being displayed may change to correspond to the slice image of the slice indicated on the indicator bar 350.

The imaging software, such as the imaging software described in U.S. Pat. Pub. 2019/0008591, herein incorporated by reference, enables the user to designate a target position, such as a tumor. After the user, for example, click on a tumor in each relevant slice, the imaging software overlays designated zone on the slice image being displayed 300 and updates the status bar 350 to show depth of tumor. This information can be used by the user to plan and define one or more trajectory for biopsy or treatment.

Where more than one needle will be used in the treatment or biopsy, there may be an indication of more than one target points or more than one insertion points to account for each of the needles used in, for example, the ablation therapy. The user can set insertion point and target point of a trajectory by, for example, clicking with a pointer element on the slice image or by touching the display screen having touch capabilities. The software overlays the insertion point(s), target point(s) and optionally a path between the two on any slices. Path may be curved when a curved probe is used.

The imaging software, in addition to or as an alternative to defining the target point 310 and an insertion point 320 for planning the insertion or insertions may also define the full region of interest 370. This can be done by requesting that the user input the information in any of the 2D images within the 3D image data to define the tumor region or region of interest.

In some embodiments, all the information defining the target point, insertion points, and optionally region of interest is specifically defined by the user. In other embodiments, some of this information can be obtained through an algorithm. For example, the user can indicate the tumor on one slice and the algorithm defines the dimensions of the region of interest based on the tumor boundary. In another example, the user defines a single target point and the format for multiple probes (e.g., the format for three probes is a triangular pattern, centered around the selected target point). In this example, the display may be either the single target point or the three distinct points defined by the triangle and the distance between the probes (see U.S. Pat. Pub. 2019/0008591).

When the procedure is an ablation, the user may select probe type, size, length, power, duration and the number of probes. Then, software can overlay expected ablation zone on the slice image as well. Users are able to compare expected ablation zone and designated tumor on each slice.

This invention can be used in conjunction with a needle guidance device that is used to guide one or more needles in a percutaneous procedure. The device includes fiducial markers, which may be visible in the display. Because they are placed uniquely in 3D coordinates, software is able to register the device in, e.g., CT images. This software updates the bar to show slices where fiducial markers exist. Software may overlay reachable area when users use the device.

Figure 4A:
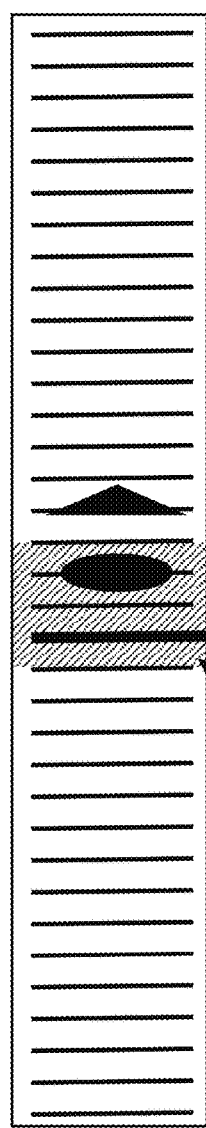
FIGS. 4(A), 4(B) and 4(C) are illustrations of different embodiments of the indicator bar.

In some embodiments, the indicator bar 350 may have more or less information and indicated in a variety of manners. For example, the location of the slice image in the 3D image data set 360 is indicated by an arrow in FIG. 4(A) and a thicker line in FIG. 4(B). The depth of the region of interest 370 is also shown, along with indicators for the target point 310 and the insertion point 320.

Figure 4B:
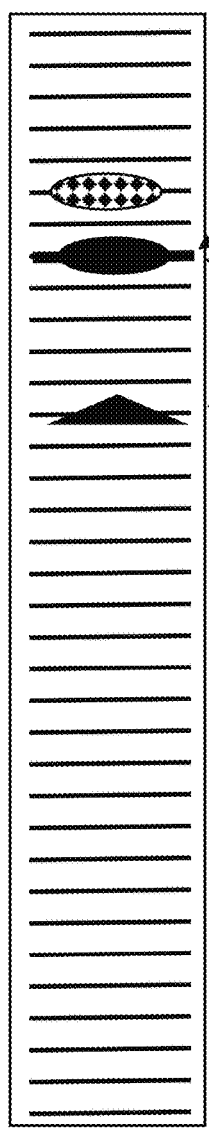
Figure 4C:
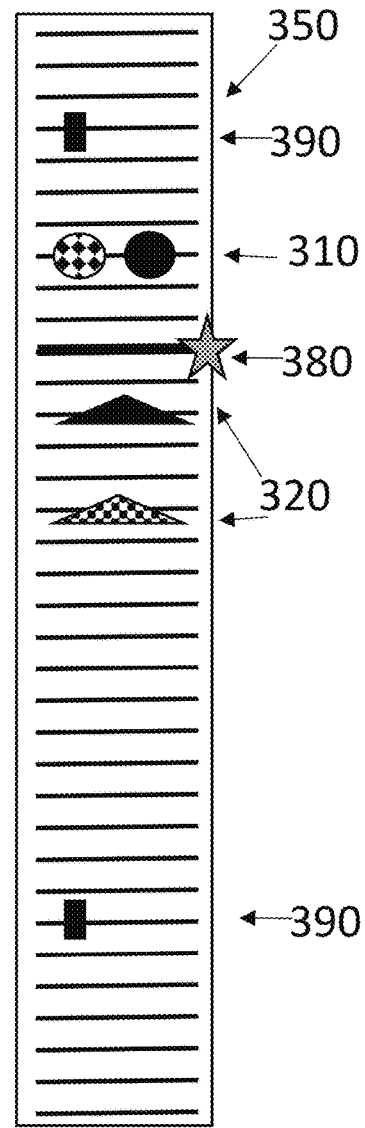

In the embodiment exemplified by FIG. 4(B), the indicator bar 350 has two separate target points 310. These are indicated by ovals as well as by numerical labels. Similarly, FIG. 4(C) depicts two separate target points 310 that, in this embodiment, occur on the same slice. The two separate targets correlate with two separate insertion points 320. This embodiment also provides an indication of a "favorite" or interesting slice 380 that may be defined by the user.

Similar to the various means of identification of the current slice 360, target points 310, insertion points 320, region of interest 370, favorite slice 380, fiducial marker 390, etc., other means may be equally applicable. For example, color can be used to distinguish and provide information about the various features on the indicator bar 350.

Information provided in the slice image 300 may include the insertion point, the region of interest, the region of interest, an ablation zone, a reachable zone (e.g., the volume of tissue reachable by a specified needle via the system from the defined insertion point). Probe (e.g., needle) trajectories as planned or as executed may be indicated as well. Fiducial markers, either detected automatically or manually may also be provided.

In some embodiments, information pertaining to slices not being displayed may also be provided in the slice image 300. For example, a probe trajectory may continue through multiple slices (three in FIG. 4(A) and eight in FIG. 4(B). This may be indicated, for example, a solid line for the probe trajectory in the displayed slice and a transparent, grey, or dashed line for the probe trajectory as it travels through a non-displayed slice. Additionally, if a curved probe is to be used, a curved trajectory may be indicated by a similar means.

In yet other embodiments, the location of the fiducial markers 390 within the three-dimensional image set may be displayed in the indicator bar 350. Other information that may be included in the indicator bar includes grids, gridlines, etc.

Figure 5:
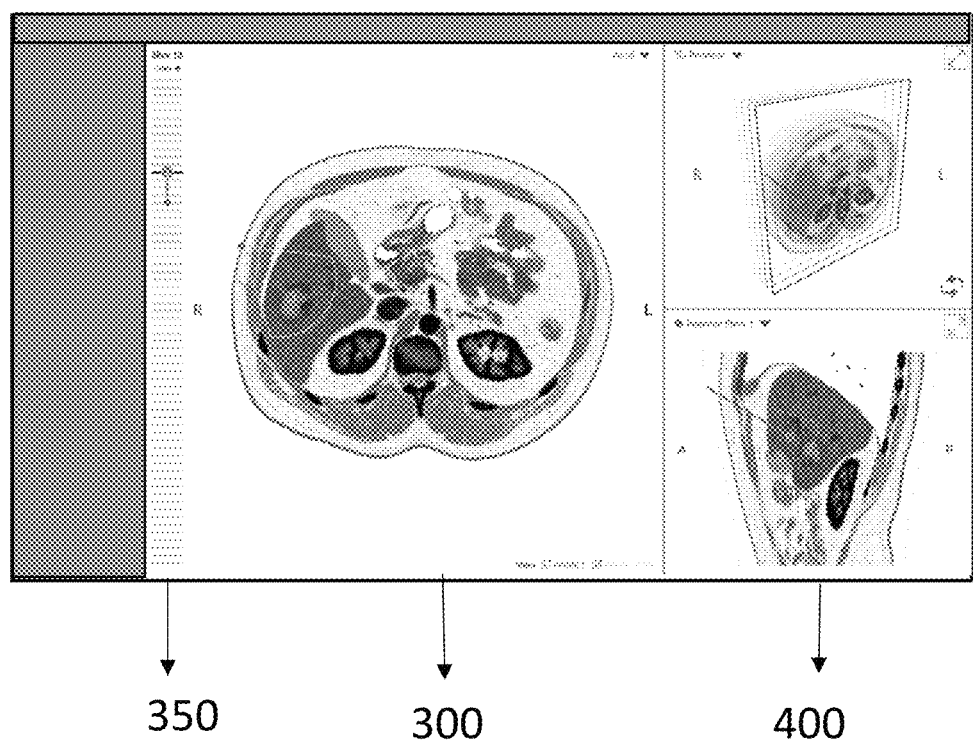
FIG. 5 is an exemplary screen shot of a planning software providing a CT scan including an overlay providing 3D information.

FIG. 5 is a screen shot of the output of an imaging software system showing a 2D image slice 300 and an indicator bar 350. Additional views of the slice image are shown 400 (e.g., an insertion plane view, a 3D view, and/or a sagittal view) as well as additional information for planning and surgery. In this case, the target point 310 is shown as a tumor in the object to be treated (i.e., the liver) with a proposed insertion point 320 for needle entry for an ablation therapy. In some embodiments, the user scans through the various slice images by, for example, clicking with a pointing device on the location of the indicator bar 350 indicating the slice to be viewed. In this instance, when a different slice is selected, both the image slice 300 displayed as well as the additional view of the image slice 400 displayed are the slice indicated by the location on the indicator bar. Alternatively, the user may scroll through the images of the two-dimensional image slices from within the main viewing window 300 or an additional window view 400.

The horizontal lines on the indicator bar shown in FIG. 5 indicate each image slice within the three-dimensional image set. The slice width of the two-dimensional images within the three-dimensional image set is indicated by the spacing of the horizontal lines within the indicator bar. If the image set is created having, for example, 2 mm slices instead of 5 mm slices, the number of horizontal lines indicating the number of two-dimensional image slices will be greater.

Figure 6:
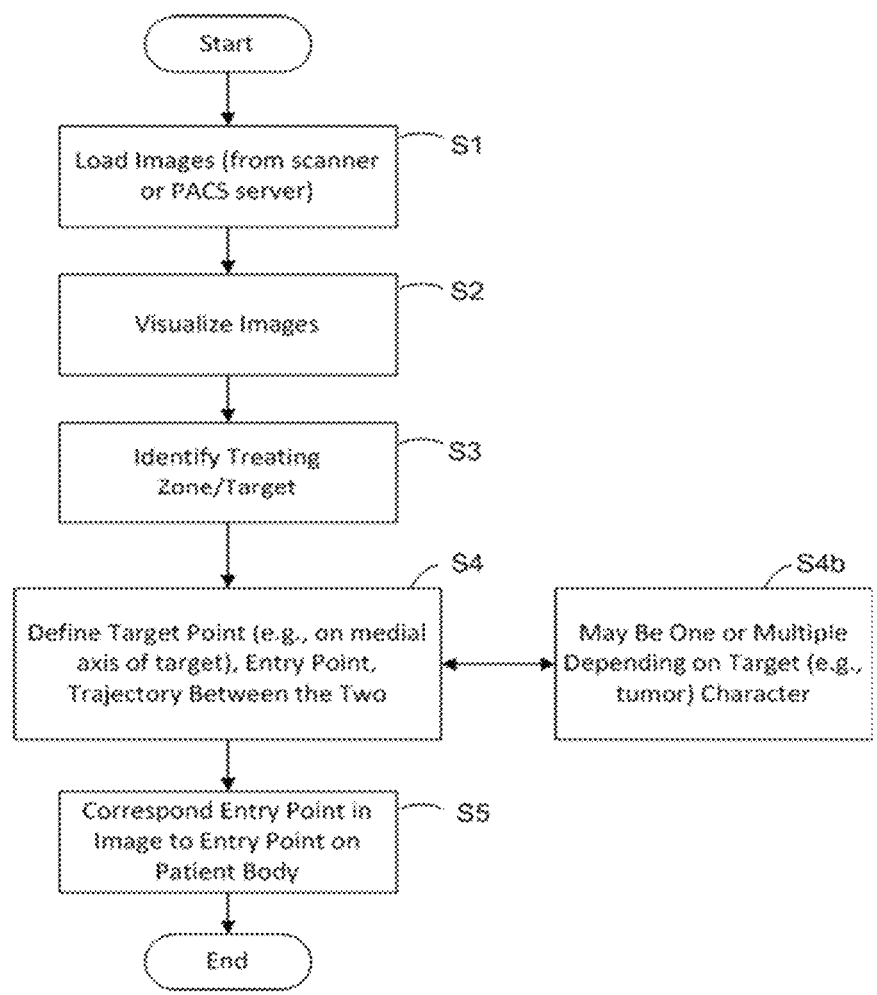
FIG. 6 is a flow chart showing at least one embodiment of a method for performing ablation and/or needle guidance planning and/or performance in accordance with one or more aspects of the present disclosure.

In an exemplary ablation procedure descried in FIG. 6, the clinician may use the imaging software system for processes including ablation planning and performance steps, including, but not limited to, one or more of the following: (i) loading images (e.g., from a scanner, a PACS or other scanning device/system, or using a fresh or newly scanned image) (see step S1 in FIG. 6); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by using the indicator bar as described herein to visually move through the 3D data set and display the reformatted slices in the 3D view; etc.)) (see step S2 in FIG. 6); (iii) identifying a region of interest, which, for ablation, can be treating zone or target (e.g., a lesion or tumor) (see step S3 in FIG. 6); (iv) defining a target point, an insertion or entry point and a trajectory between the target and insertion points (see step S4 in FIG. 6) (as shown in step S4b, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 6).

Once the region of interest or target point and the insertion point are determined, the indictor bar will display the location of these features within the three-dimensional image set. The clinician is then free to move through the three-dimensional image set by using the information provided in the indicator bar to, for example: verify the accuracy of the location of these features on the images, determine if the margin is acceptable, view the trajectory (or trajectories), search the images for the location of other key features (e.g., blood vessels or bile ducts), or determine the number of needles and/or size of ablation therapy required.

Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). The target point or points that is clinically the best choice (e.g., mathematically, statistically, etc.) may be selected via an algorithm for placement of the target point(s). In one or more embodiments, target point(s) may be determined by finding or determining a medial axis or center line of the target or treating zone (see step S4 of FIG. 6).

Figure 7:
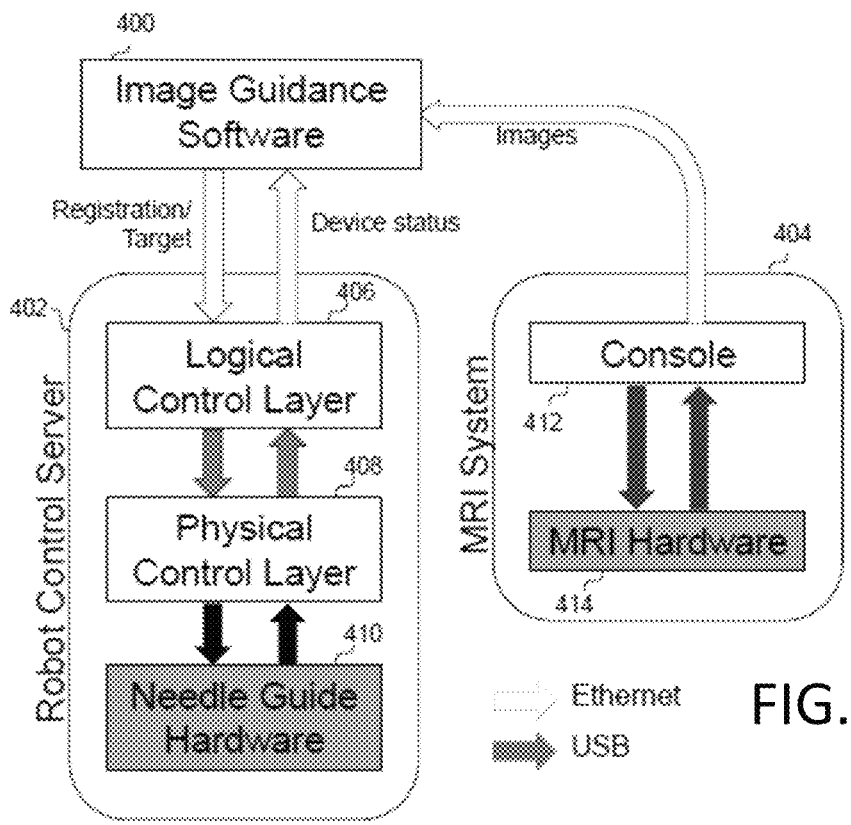
FIG. 7 illustrates an example system diagram for a needle guide device system including image software, robot control server of a needle guide device, and MRI system including an MRI scanner in accordance with some embodiments.

FIG. 7 illustrates an example system diagram for a needle guide device including imaging software, robot control server of a needle guide device, and MRI system including an MRI scanner in accordance with some embodiments. FIG. 7 represents one example of a system for a needle guide device, but the present disclosure is not limited to such a system. For example, according to some embodiments, the needle guide device is a manually operated device. For example, needle guide devices that may be used in combination with systems described herein are described in U.S. Pat. No. 9,222,996 and in U.S. patent application Ser. No. 15/808,703, both of which are herein incorporated by reference in their entirety. Any suitable needle guide device may be used in conjunction with the embodiments of the present disclosure. The following description of FIG. 7 is merely an example of a needle guide system, which may be used in conjunction with the systems and methods described herein.

Robot Control Software

In some embodiments, a software system is provided that has three layers of components including, image guidance software 400, logical control layer 406, and physical control interface 408 (FIG. 7). Those components are implemented as independent software processes, and communicate with each other via, for example, Ethernet and Universal Serial Bus (USB). However, in other embodiments, two more of these components are integrated into a single software process.

The details of those three components are as follows:

Image Guidance Software

The image guidance software 400 is the top layer component in the system and is exemplified in FIG. 7. The image guidance software 400 works, for example, as a primary user interface for the physician and/or operator. It is implemented as described herein as a plug-in module for 3D Slicer, open-source medical image computing software and, through this or other software, receives images from the MRI System 404, which includes the console 412 and MRI hardware 414, which includes an MRI scanner. The image guidance software 400 assists the physician in performing the following tasks.

Needle Placement Planning.

The physician can define a trajectory of needle placement by specifying the targets and skin entry point on the planning image. The software displays a section of the planning image along any plane and allows the physician to specify the points by, for example, clicking on it with a mouse. Once the trajectory has been defined, it can re-slice the 3D image with a plane along the trajectory so that the physician can find any critical structures and obstacles around the path (see FIG. 1). The defined trajectory is transferred to the robot control server 402. The final decision to move the actuator, however, may be made by the physician standing by the gantry; the actuators can be powered on when the physician presses down a footswitch.

Device-to-Image Registration.

The software can automatically register the needle guide device to the image coordinate system. A registered device model is overlaid on the planning image data and its accessible range/reachable zone is presented on the image, so that the operator can confirm that the all targets are in range (see FIG. 1, item 103). Information is transferred to the robot control server 402 over the network using, for example, the OpenIGTLink protocol.

Monitoring and Confirmation of Probe Placement.

The software can be used to visualize the current position and orientation of the device with a 3D model overlaid on the images during planning for or performance of a procedure. In addition, it also can display confirmation images that show the probe inserted into the patient with the planned trajectory and target (see FIG. 1). Those features allow the physicians to monitor the device and confirm the probe placement.

Logical Control Layer

The Logical Control Layer (LCL) 406 sits in the middle layer of the system and interfaces the image guidance software 400 and low-level physical control layer (PCL) 408. This layer of the robot control server 402 can encapsulate the hardware and the kinematic structure of the device, and provide a device-independent application program interface (API) to the upper layer. Therefore, the LCL 406 consists of the following subcomponents:

TCP/IP Network Interface to the Upper Layer.

Through this interface, the LCL 406 receives commands to the hardware from the upper layer including the target position, and provides the current status of the hardware (410) to the upper layer including the current position of the needle guide, and the status of the device. It also provides the required needle insertion depth as a result of kinematics computation (see Kinematics engine below) to the upper layer. In some embodiments, the network interface is compliant with the OpenIGTLink protocol, and thus it can communicate with software compatible with OpenIGTLink.

Kinematics Engine.

In some embodiments, the hardware-independent commands received from the upper layer are translated into the target positions of individual actuators based on the kinematics of the needle guide device, and sent to the PCL 408. Moreover, in some embodiments, current positions of individual actuators received from the PCL 408 are translated to the position and orientation of the needle guide and sent to the upper layer.

Serial Interface to the Lower Layer.

The LCL 406 communicates with the lower layer subcomponent through a universal serial bus (USB). Through this exemplary interface, target positions of individual actuators and other device-specific commands are sent to the PCL 408, while the current status of the device and the encoder readings of individual actuators are sent to the image guidance software 400. The information exchanged through this interface is dependent on the kinematic structure, but independent from the physical hardware (e.g. motor drivers and encoders).

Physical Control Layer

The role of the Physical Control Layer (PCL) 408 is to provide an interface that is independent from the physical input/output (I/O), but dependent on the kinematic structure. In some embodiments, the PCL 408 runs on a Linux-based embedded computer equipped with a USB interface for the communication with the LCL 406, and a digital input/output interface for reading inputs from encoders and footswitch and giving the target speeds of individual motors to the motor drivers. Once the controller receives target positions for individual actuators, it performs closed-loop PID control of individual motors. Throughout this process, the PCL 408 can optionally keep sending current positions and other device status.

Computing System

Figure 8:
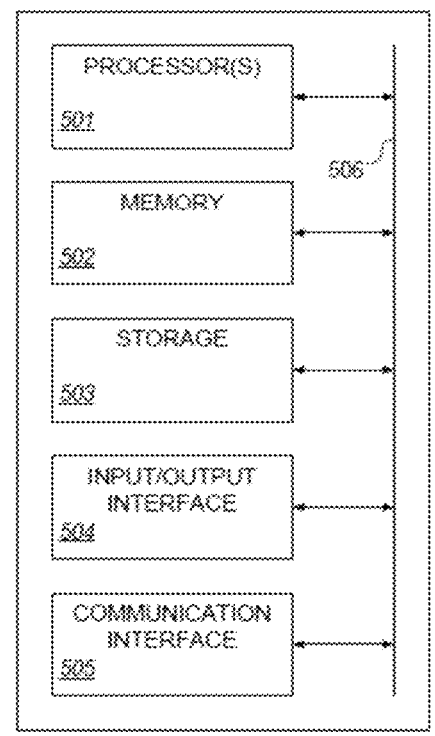
FIG. 8 illustrates an example computing system in accordance with some embodiments.

FIG. 8 provides a computing system for the device and software as described herein. In some embodiments, the computing system 500 includes the image guidance software described herein. For example, in some embodiments, the computing system 500 may include the image guidance software 400 of FIG. 7, components of which are described in detail herein. The various programs and data—for example, software modules, libraries, tools, user interface elements, or other components—of the image guidance software reside in the computing system 500 in any suitable manner, in accordance with various embodiments. For example, these components may reside in one or multiple storage locations. The components of the image guidance software may be provided as part(s) of a single software application or as a plurality of stand-alone software applications. The computing system 500 provides access to the image guidance software. In some embodiments, the image guidance software executing on the computing system 500 performs one or more steps of one or more methods described or illustrated herein, or provides functionality described or illustrated herein. For example, programs of the image guidance software may include instructions that, when executed by one or more processors, cause the computing system 500 to perform the process described herein.

The term computing system as used herein includes but is not limited to one or more software modules, one or more hardware modules, one or more firmware modules, or combinations thereof, that work together to perform operations on electronic data. The physical layout of the modules may vary. A computing system may include multiple computing devices coupled via a network. A computing system may include a single computing device where internal modules (such as a memory and processor) work together to perform operations on electronic data. In some embodiments, a single computing system 500 includes the image guidance software.

In some embodiments, the image guidance software executing on the computing system 500 interacts with the robot control server 402 and with the MRI System 404. The computing system 500 may use any suitable protocol(s), standard(s), data exchange format(s), or combination(s) of these, to communicate with and send/receive information to/from one or more of the systems described herein. The computing system 500 may send and receive information and requests using OpenIGTLink. The computing system 500 can receive, send, and store DICOM (Digital Imaging and Communications in Medicine) files and data. For example, the computing system 500 may receive a medical image from the MRI System 404. Additionally, the computing system 500 may send HTTP requests and provide HTTP responses. The responses may include Hyper Text Markup Language (HTML) files, or other suitable files, executable code, such as JAVASCRIPT, form elements, images, or other content. One or more elements of the content may be stored at the computing system 500. In some embodiments, the computing system 500 uses Simple Object Access Protocol (SOAP) to receive and send messages.

The computing system 500 as shown in FIG. 8 includes one or more processor(s) 501, memory 502, storage 503, an input/output (I/O) interface 504, a communication interface 505, and a bus 506. The computing system 500 may take any suitable physical form. For example, and not by way of limitation, the computing system 500 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, PDA, a tablet computer system, one or more servers, a workstation, or a combination of two or more of these. In some embodiments, the computing system 500 is unitary. In some embodiments, the computing system 500 is distributed. The computing system 500 may span multiple locations. The computing system 500 may span multiple machines.

The processor(s) 501 include hardware for executing instructions, such as those making up a computer program. The processor(s) 501 may retrieve the instructions from the memory 502, the storage 503, an internal register, or an internal cache. The processor(s) 501 then decode and execute the instructions. Then, the processor(s) 501 write one or more results to the memory 502, the storage 503, the internal register, or the internal cache. The processor(s) 501 may provide the processing capability to execute the operating system, programs, user and application interfaces, and any other functions of the computing system 500.

The processor(s) 501 may include a central processing unit (CPU), one or more general-purpose microprocessor(s), application-specific microprocessor(s), and/or special purpose microprocessor(s), or some combination of such processing components. The processor(s) 501 may include one or more graphics processors, video processors, audio processors and/or related chip sets.

In some embodiments, the memory 502 includes main memory for storing instructions for the processor(s) 501 to execute or data for the processor(s) 501 to operate on. By way of example, the computing system 500 may load instructions from the storage 503 or another source to the memory 502. During or after execution of the instructions, the processor(s) 501 may write one or more results (which may be intermediate or final results) to the memory 502. One or more memory buses (which may each include an address bus and a data bus) may couple the processor(s) 501 to the memory 502. One or more memory management units (MMUs) may reside between the processor(s) 501 and the memory 502 and facilitate accesses to the memory 502 requested by the processor(s) 501. The memory 502 may include one or more memories. The memory 502 may be random access memory (RAM).

The storage 503 stores data and/or instructions. As an example and not by way of limitation, the storage 503 may include a hard disk drive, a floppy disk drive, flash memory, an optical disc, a magneto-optical disc, magnetic tape, or a Universal Serial Bus (USB) drive or a combination of two or more of these. In some embodiments, the storage 503 is a removable medium. In some embodiments, the storage 503 is a fixed medium. In some embodiments, the storage 503 is internal to the computing system 500. In some embodiments, the storage 503 is external to the computing system 500. In some embodiments, the storage 503 is non-volatile, solid-state memory. In some embodiments, the storage 503 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. The storage 503 may include one or more memory devices. The storage 503 may store application data, program modules and other information. One or more program modules stored in the storage 503 are configured to cause various operations and processes described herein to be executed. In some embodiments, the image guidance software resides on the storage 503 and executes on the computing system 500. The storage 503 may further store other programs and/or drivers that enable various functions of the computing system 500, graphical user interface (GUI) functions, and/or processor functions. The storage 503 may also store data files including, for example, image data, user data, configuration information, GUI components, such as graphical elements or templates, or other data required by the computing system 500.

The I/O interface 504 includes hardware, software, or both providing one or more interfaces for communication between the computing system 500 and one or more I/O devices. In some embodiments, the computing system 500 includes one or more I/O devices. One or more of these I/O devices may enable communication between a person and the computing system 500. On I/O device is the input device for scrolling along the indicator bar. By way of example and not by way of limitation, an I/O device may include a keyboard, keypad, microphone, monitor, mouse, touchpad, speaker, still camera, stylus, tablet, touch screen, trackball, video camera, another suitable I/O device or a combination of two or more of these. An I/O device may include one or more sensors. In some embodiments, the I/O interface 504 includes one or more device or software drivers enabling the processor(s) 501 to drive one or more of these I/O devices. The I/O interface 504 may include one or more I/O interfaces.

In some embodiments, the computing system 500 includes a display. For example, the display may be a liquid crystal display (LCD). In some embodiments, the image guidance software running on the computing system 500 presents GUI data on the display. In some embodiments, the GUI data is presented in conjunction with medical image data. Regarding outputting signals to the display, the processor(s) 501 rasterize an image to be displayed on the display, and transfer the rasterized image to the display via the I/O interface 504. The display then displays the image, such as a GUI. The processor(s) 501 are further operable to cause other types of images, such as medical images from the MRI System 404, to be displayed on the display. The computing system 500 may receive an input signal based on user inputs at the display. For example, in some embodiments, the display includes a touch sensitive element operable to receive user inputs or commands based on the touching one or more interface elements on the display. The interface element may be a graphical object presented on the display. A user may touch the touch sensitive display with a finger, stylus, or other tool to provide a user input. When the user touches a specific region on the touch sensitive display, the processor(s) 501 are notified via the I/O interface 504 of the coordinates of the region. The processor(s) 501 determine the content of a user input based on the notified coordinates and the display contents on the display, and execute processing based on them. In some embodiments, a mouse or touchpad is used in conjunction with information presented on the display to receive user inputs and selections. For example, a cursor may be used to select one or more interface elements presented in the GUI on the display. According to various embodiments, the touch sensitive display, the cursor, or other suitable method for providing an input, is used to specify one or more location(s) on a medical image presented in the GUI on the display to indicate, for example, a target and a planned insertion point for inserting a needle into a patient.

In some embodiments, the computing system 500 includes a keyboard/keypad. User inputs may also be provided via the keyboard/keypad. When the user presses a hard key of the keyboard/keypad, the processor(s) 501 are notified via the I/O interface 504 of information indicative of the user input. The processor(s) 501 execute processing based on the notification. The hard keys and/or buttons of the keyboard/keypad may be arranged in any suitable configuration. Furthermore, the input structures may include buttons, keys, switches, control pads, or other suitable structure, depending on specific implementation requirements.

The communication interface 505 includes hardware, software, or both providing one or more interfaces for communication (such as, for example, packet-based communication) between the computing system 500 and one or more other computing systems or one or more networks. As an example and not by way of limitation, the communication interface 505 may include a network interface card (NIC) or a network controller for communicating with an Ethernet or other wire-based network or a wireless NIC (WNIC) or wireless adapter for communicating with a wireless network, such as a WI-FI network. This disclosure contemplates any suitable network and any suitable communication interface 505 for it. As an example and not by way of limitation, the computing system 500 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system 500 may communicate with a wireless PAN (WPAN) (such as, for example, a Bluetooth WPAN or an ultra-wideband (UWB) network), a WI-FI network, a WI-MAX network, a cellular telephone network (such as, for example, a Global System for Mobile Communications (GSM) network), or other suitable wireless network or a combination of two or more of these. The computing system 500 may include any suitable communication interface 505 for any of these networks, where appropriate. The communication interface 505 may include one or more communication interfaces 505.

The bus 506 interconnects various components of the computing system 500 thereby enabling the transmission of data and execution of various processes. The bus 506 may include one or more types of bus structures including a memory bus or memory controller, a peripheral bus, and a local bus using any of a variety of bus architectures.

The above description serves to explain principles of the present disclosure; but the present disclosure should not be limited to the examples described above. For example, the order and/or timing of some of the various operations may vary from the examples given above without departing from the scope of the present disclosure. Further, by way of example, the type of network and/or computing systems may vary from the examples given above without departing from the scope of the present disclosure. Other variations from the examples given above may also exist without departing from the scope of the present disclosure. While particular examples of GUIs are illustrated, it will be understood that various other implementations of GUIs are within the scope of the present disclosure. For example, various features of the illustrated examples could be modified, rearranged, or removed, or one or more features could be added without departing from the scope of the present disclosure.

The scope of the present disclosure includes a computer-readable medium storing instructions that, when executed by one or more processors, cause the one or more processors to perform one or more embodiments described herein. Examples of a computer-readable medium include a hard disk, a floppy disk, a magneto-optical disk (MO), a compact-disk read-only memory (CD-ROM), a compact disk recordable (CD-R), a CD-Rewritable (CD-RW), a digital versatile disk ROM (DVD-ROM), a DVD-RAM, a DVD-RW, a DVD+RW, magnetic tape, a nonvolatile memory card, and a ROM. Computer-executable instructions can also be supplied to the computer-readable storage medium by being downloaded via a network.

While the present disclosure has been described with reference to exemplary embodiments, it is to be understood that the present disclosure is not limited to the exemplary embodiments described.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An image processing apparatus comprising a processor that operates to:
   acquire a three-dimensional image set comprising a stack of two-dimensional image slices;
   acquire the location of at least one region of interest or at least one target point in the three-dimensional image set;
   acquire the location of at least one insertion point in the three-dimensional image set;
   cause a display to display a first two-dimensional image slice from the three-dimensional image set; and
   cause the display to display, concurrent with the first two-dimensional image slice, an indicator bar, wherein the indicator bar indicates:
      the location of the first two-dimensional image slice within the three-dimensional image set,
      the location of the at least one region of interest or at least one target point within the three-dimensional image set, and
      the location of the insertion point within the three-dimensional image set.

2. The image processing apparatus of claim 1, wherein the processor generates and displays on the first two-dimensional image slice at least one of:
   a reference trajectory connecting the target point and the insertion point,
   a reachable zone presenting a volume reachable by a tool from the insertion point, and
   the location of one or more fiducial markers on the first two-dimensional image slice.

3. The image processing apparatus of claim 1, wherein the at least one region of interest or at least one target point in the image and the at least one insertion point are determined in response to receiving a user input for selecting a position in the displayed first two-dimensional image slice.

4. The image processing apparatus of claim 1, wherein the three-dimensional image set is an ultrasound image set, a computer tomography (CT) image set, or a magnetic resonance (MR) image set.

5. The image processing apparatus of claim 1, where a digital representation of a needle guide device is overlaid on the first two-dimensional image slice.

6. The image processing apparatus of claim 1, wherein the processor acquires the location of the at least one region of interest or at least one target point and the at least one insertion point in the three-dimensional image set from one or more user input device.

7. The image processing apparatus of claim 1, wherein the processor displays the region of interest and the insertion point superimposed on the displayed first two-dimensional image slice.

8. The image processing apparatus of claim 1, further comprising an input means for inputting a desired viewing location that includes a second two-dimensional image slice within the three dimensional image set, and wherein the processor further causes the display to display the second two-dimensional image slice from the three-dimensional image set.

9. An image processing apparatus for supporting a needle placement process, planning, or assessment comprising:
   a processor that operates to:
      acquire a three-dimensional image set comprising a stack of two-dimensional image slices;
      acquire the location of at least one region of interest or at least one target point in the three-dimensional image set;
      acquire the location of at least one insertion point in the three-dimensional image set;
      cause a display to display a first two-dimensional image slice from the three-dimensional image set; and
      cause the display to display, concurrent with the first two-dimensional image slice, an indicator bar, wherein the indicator bar indicates:
         the location of the first two-dimensional image slice within the three-dimensional image set,
         the location of the at least one region of interest or at least one target point within the three-dimensional image set, and
         the location of the insertion point within the three-dimensional image set, and wherein the processor causes the display to display a second two-dimensional image from the three-dimensional image set.

10. A method of performing planning or treatment for a percutaneous probe treatment, comprising:
   acquiring a three-dimensional image set comprising a stack of two-dimensional image slices;
   acquiring the location of at least one region of interest or at least one target point in the three-dimensional image set;
   acquiring the location of at least one insertion point in the three-dimensional image set;
   causing a display to display a first two-dimensional image slice from the three-dimensional image set; and
   causing the display to display, concurrent with the first two-dimensional image slice, an indicator bar, wherein the indicator bar indicates:
      the location of the first two-dimensional image slice within the three-dimensional image set,
      the location of the at least one region of interest or at least one target point within the three-dimensional image set, and
      the location of the insertion point within the three-dimensional image set.

11. The method of claim 10, further comprising causing the processor to display, on the first two-dimensional image slice, when applicable, at least one of:
   a reference trajectory connecting the target point and the insertion point,
   a reachable zone presenting a volume reachable by a tool from the insertion point, and
   the location of one or more fiducial markers on the first two-dimensional image slice.

12. The method of claim 10, further comprising receiving at least one user input to acquire the location of at least one region of interest or at least one target point in the three-dimensional image set and the at least one insertion point.

13. The method of claim 10, wherein acquiring the three-dimensional image set comprises acquiring at least one of an ultrasound image set, a computer tomography (CT) image set, and a magnetic resonance (MR) image set of the object to be treated.

14. The method of claim 10, further comprising overlaying a digital representation of a needle guide device on the first two-dimensional image slice.

15. The method of claim 10, further comprising changing the display of the first two-dimensional image slice to correspond to a position defined by an input device on the indicator bar.

16. An imaging server storing an imaging application having instructions that, when executed by a processor, cause the imaging server to perform the method according to claim 10.

17. A non-transitory computer-readable storage medium storing an imaging application to cause an imaging server to perform the method according to claim 10.

* * * * *